(12) United States Patent
DeToro et al.

(10) Patent No.: US 7,682,323 B2
(45) Date of Patent: Mar. 23, 2010

(54) COORDINATED CUFF DISPLACEMENT IN AN ORTHOTIC DEVICE

(75) Inventors: William W. DeToro, Poland, OH (US);
Brian S. Perala, Warren, OH (US);
William A. DeToro, Poland, OH (US);
Jack N. Huey, Poland, OH (US)

(73) Assignee: Anatomical Concepts, Inc., Poland, OH (US)

( * ) Notice: Subject to any disclaimer, the term of this patent is extended or adjusted under 35 U.S.C. 154(b) by 0 days.

(21) Appl. No.: 12/384,300

(22) Filed: Apr. 2, 2009

(65) Prior Publication Data
US 2010/0016773 A1    Jan. 21, 2010

Related U.S. Application Data

(63) Continuation-in-part of application No. 12/220,078, filed on Jul. 21, 2008.

(51) Int. Cl.
A61F 5/00 (2006.01)
(52) U.S. Cl. .............................. 602/16; 602/20; 602/21; 602/23
(58) Field of Classification Search ...................... 602/5, 602/16, 20–23, 26–27; 128/882; 482/45
See application file for complete search history.

(56) References Cited

U.S. PATENT DOCUMENTS

| | | |
|---|---|---|
| 183,376 A | 10/1876 | Darrach |
| 1,257,297 A | 2/1918 | Brown |
| 1,851,241 A | 3/1932 | Dresser |
| 2,516,253 A | 7/1950 | Pieterick |
| 2,559,473 A | 7/1951 | Slodek, Sr. |
| 2,591,373 A | 4/1952 | Petruch |
| 2,943,622 A | 7/1960 | Nelson |
| 3,026,869 A | 3/1962 | Peach |
| 3,669,105 A | 6/1972 | Castiglia |
| 3,779,654 A | 12/1973 | Horne |
| 3,923,047 A | 12/1975 | Chant |
| 4,337,764 A | 7/1982 | Lerman |
| 4,388,920 A | 6/1983 | Hajost et al. |
| 4,502,472 A | 3/1985 | Pansiera |
| 4,928,676 A | 5/1990 | Pansiera |
| 4,982,732 A | 1/1991 | Morris |
| 5,088,479 A | 2/1992 | Detoro |
| 5,135,469 A | 8/1992 | Castillo |
| 5,399,149 A | 3/1995 | Frankowiak et al. |
| 5,486,157 A | 1/1996 | DiBenedetto |
| 5,545,127 A | 8/1996 | DeToro |
| 5,624,389 A | 4/1997 | Zepf |
| 5,707,347 A | 1/1998 | Bixler |
| 5,776,086 A | 7/1998 | Pansiera |
| 5,848,979 A | 12/1998 | Bonutti et al. |
| 5,873,847 A | 2/1999 | Bennett et al. |

(Continued)

Primary Examiner—Michael A. Brown
(74) Attorney, Agent, or Firm—Robert J. Herberger (57) ABSTRACT

An orthotic device for a human body joint at which a body appendage pivots includes a first member extending along the appendage on a first side of the joint, a second member extending along the appendage on a second side of the joint opposite the first side, a connection joining the first member and the second member and having an axis about which the members articulate, a cuff spaced from the axis, and a mechanism displacing the cuff along one of the members in response to articulating the device at the connection.

22 Claims, 12 Drawing Sheets

U.S. PATENT DOCUMENTS

| | | | |
|---|---|---|---|
| 5,908,398 A | 6/1999 | DeToro | |
| 5,954,678 A | 9/1999 | Cruz | |
| 6,045,520 A | 4/2000 | Buckley | |
| 6,090,057 A | 7/2000 | Collins et al. | |
| 6,113,562 A | 9/2000 | Bonutti et al. | |
| 6,245,034 B1 | 6/2001 | Bennett et al. | |
| 6,302,858 B1 | 10/2001 | DeToro et al. | |
| 6,350,246 B1 | 2/2002 | DeToro et al. | |
| 6,375,632 B1 | 4/2002 | Albrecht et al. | |
| 6,488,644 B1 | 12/2002 | Ostrom et al. | |
| 6,533,741 B1 | 3/2003 | Lee et al. | |
| 6,589,195 B1 | 7/2003 | Schwenn et al. | |
| 6,793,638 B1 | 9/2004 | DeToro et al. | |
| 6,821,261 B2 | 11/2004 | Doty et al. | |
| 6,981,957 B2 | 1/2006 | Knecht et al. | |
| 6,993,808 B1 | 2/2006 | Bennett et al. | |
| 7,011,641 B1 | 3/2006 | DeToro et al. | |
| 7,083,583 B2 | 8/2006 | Opahle et al. | |
| 7,112,179 B2 | 9/2006 | Bonutti et al. | |
| 7,112,181 B1 | 9/2006 | DeToro et al. | |
| 7,122,016 B1 | 10/2006 | DeToro et al. | |

COORDINATED CUFF DISPLACEMENT IN AN ORTHOTIC DEVICE

This is a continuation-in-part application of application Ser. No. 12/220,078, filed Jul. 21, 2008.

BACKGROUND OF THE INVENTION

1. Field of the Invention

This invention relates generally to an orthotic device that provides multiple, adjustable functions for controlling the angular position and motion of a joint, and, more particularly, for coordinating movement of a cuff with flexure of the orthotic device.

2. Description of the Prior Art

An orthotic is a device, such as a brace or splint, for supporting, immobilizing, or treating muscles, joints, or skeletal parts, which are weak, ineffective, deformed, or injured. To assist in restoring a joint of the human body to normal, effective function, it may be preferred that the joint be restricted for a period by an orthotic, which imposes a fixed pivoted position. Or, an orthotic may be needed that permits adjustable angular displacement of the joint, which is retained for a period by the orthotic and gradually increased at intervals to improve the pivotal range of use.

An orthotic leg device, for example, can typically provide one or two of five common functions: i) free motion about the knee joint as illustrated in U.S. Pat. No. 3,779,654 to Horne and U.S. Pat. No. 3,669,105 to Castiglia; ii) a ring drop lock joint to keep the knee joint extended as shown in U.S. Pat. No. 3,923,047 to Chant and U.S. Pat. No. 4,928,676 to Pansiera; iii) a step-lock ratchet joint to support the strength of the knee as it extends to various angular positions as seen in U.S. Pat. Nos. 4,502,472 and 5,776,086 to Pansiera; iv) a range of motion joint as disclosed in U.S. Pat. No. 4,337,764 to Lerman and U.S. Pat. No. 4,982,732 to Morris; or v) a variable, fixed position joint that can be locked in select positions as seen in U.S. Pat. No. 4,388,920 to Hajost et al. and U.S. Pat. No. 7,122,016 to DeToro et al. Each of these five different functioning knee braces have a specific use during therapy of a patient. In each case, a different brace is typically required.

A need exists, therefore, for one orthotic device that provides these multiple functions, including: a fixed position by releasing an attachment, changing the angular displacement of the orthotic about the axis to a new, desired orientation, and securing the orthotic to that desired position; a limited range of movement about the axis that can be adjusted easily and remain limited reliably by mutual contact between stop surfaces located on opposite sides of the axis; and a free range of movement about an axis. Further, an orthotic device that can be adjusted to multiple, mutually spaced ratcheted locations to enhance the range of flexibility and use of the joint provides an added advantage.

SUMMARY OF THE INVENTION

An orthotic device for a joint of a human body at which a body appendage pivots include a first member extending along the appendage on a first side of the joint, a second member extending along the appendage on a second side of the joint opposite the first side, a connection joining the first member and the second member and having an axis about which the members articulate, a cuff spaced from the axis, and a mechanism displacing the cuff along one of the members in response to articulating the device at the connection.

When the leg is contracted, the ratchet will lock in angular increments and stop re-contracture until the leg reaches the straight position, whereupon the brace prevents contracture and extension (i.e. step-lock ratchet function).

If the ratchet function is released, the leg can be contracted at the knee. More specifically, the ratcheting function can be locked out temporarily, such as when the person using the brace wishes to sit down. Notably, the ratchet re-engages automatically when the brace is fully extended, or it re-engages manually by applying slight upward pressure on the ratchet when in the locked out position (i.e. drop lock function).

By disengaging the ratchet completely, the joint of the orthotic device can turn freely about the lateral axis upon loosening lock nuts (i.e. free motion function).

Further, the brace can be adjusted to provide a range of pivoting motion about the joint by adjusting locknuts a predetermined amount corresponding to the desired flexion limit angle. The flexion limit angle is set first by adjusting the flexion limiting lock nut, and an extension angular limit is set by tightening or loosening the other lock nut (i.e. range of motion function). Further yet, the brace can be returned to the free motion function upon completely loosening both lock nuts, or the brace can be locked in any position by placing the brace in the desired angular flexion and tightening both lock nuts (i.e. variable, fixed position function).

Still further, the brace accommodates contraction and expansion of the muscles and skin that accompany flexion and extension of the knee joint, by providing an upper member having a thigh cuff attachable to the thigh that slides in an upper pocket, a lower member having a calf cuff attachable to the calf that slides in a lower pocket, so that the positions of the thigh and calf cuffs remain unchanged relative to the extension and contraction of the leg. The position of the joint, therefore, remains unchanged at the back of the knee due to the tendency of the springs to keep the brace cuffs at their secured positions.

The scope of applicability of the preferred embodiment will become even more apparent from the following detailed description, claims and drawings. It should be understood, that the description and specific examples, although indicating the preferred embodiments of the invention, are given by way of illustration only. Various changes and modifications to the described embodiments and examples will become apparent to those skilled in the art.

DESCRIPTION OF THE DRAWINGS

Having generally described the nature of the invention, reference will now be made to the accompanying drawings used to illustrate and describe the preferred embodiments thereof. Further, these and other advantages will become apparent to those skilled in the art from the following detailed description of the embodiments, when considered in light of these drawings in which.

DESCRIPTION OF THE PREFERRED EMBODIMENT

Referring first to FIGS. 1 through 4, an orthotic device 10 includes an upper member 12 and a lower member 14, which are interconnected by a ratcheting joint 15. Each member 12, 14 is preferably formed of aluminum or another structural material having density, strength and endurance comparable to those of aluminum.

The upper member 12 includes two lugs 16, 18, spaced mutually along a lateral axis 20, each lug having a hole 22, 23, in which screw threads are tapped. Preferably, the screw threads in holes 22, 23 are right-hand threads. The outer surface of each lug 16, 18 is counterbored at the respective hole. A plastic thigh cuff 24, whose front surface conforms to the contour of the back of the human thigh, is formed at its back surface with a longitudinal pocket 26. The upper member 12 is inserted into pocket 26 and retained there by threaded attachments 28, each attachment comprising a screw which passes through a slotted hole 30 in member 12 and a nut that engages the screw and contacts the outer surface of pocket 26. Tension springs 32, 33, each have an end secured to the upper member 12 by engaging a hole 34, and the opposite end secured to the thigh cuff 24 at attachment element 35, thereby permitting member 12 to move elastically along a longitudinal axis 36 relative to the thigh cuff 24. Multiple VELCRO straps 38, 40 secure the thigh cuff 24 to the leg of the person wearing the brace 10. A threaded hole 42 is tapped in the upper member 12, and an elongated hole 44 is formed at a lower elevation than that of the threaded hole 42. The lower edge 46 of the upper member 12 faces the lower member 14.

Referring now to FIGS. 1 and 5 through 8, the lower member 14 includes: a central lug 50 located between lugs 16, 18 and formed with an unthreaded hole 52, which is aligned with lateral axis 20 and threaded holes 22, 23; a series of ratchet teeth 54, spaced mutually about axis 20; a stop surface 55; and a slot 56. Two tapped holes 58, 59, directed toward axis 20, are formed in lug 50. A calf cuff 60, whose front surface conforms to the contour of the calf of the human leg, is formed at its back surface with a longitudinal lower pocket 62. The lower member 14 is inserted into pocket 62 and retained there by threaded attachments 64, 65, each attachment comprising a screw which passes through a slotted hole 66 in member 14 and a nut that engage the screw and contacts the outer surface of pocket 62. Tension springs 68, 69, each have one end secured to the lower member 14 by engaging a hole 67, and the opposite end secured to the calf cuff 60, permitting member 14 to move along longitudinal axis 36 relative to the calf cuff 60. Multiple VELCRO straps 70, 72 secure calf cuff 60 to the patient's leg. A hole 74 is drilled in the lower member 14 to lock the cuff in a shortened position if necessary.

Figure 1:
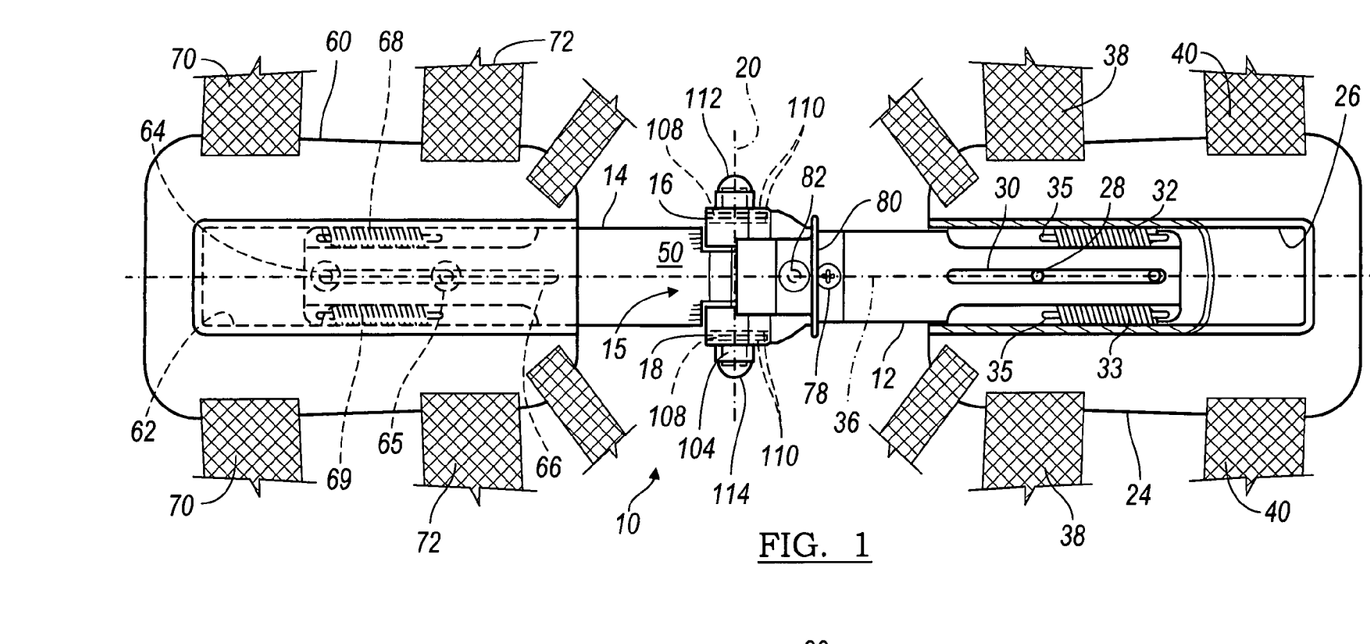
FIG. 1 is a rear view of a multiple function leg orthotic device.
Figure 2:
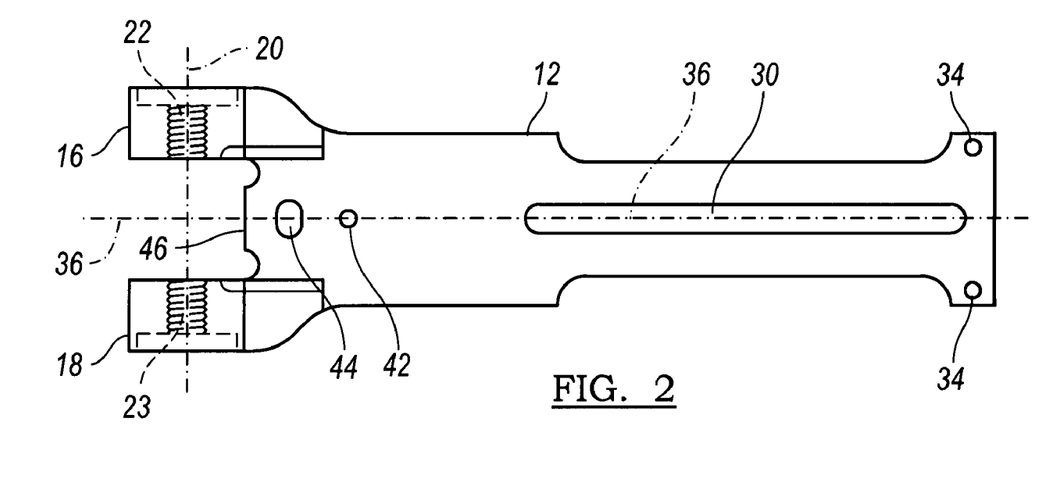
FIG. 2 is a top view of an upper member of the orthotic device of FIG. 1.
Figure 3:
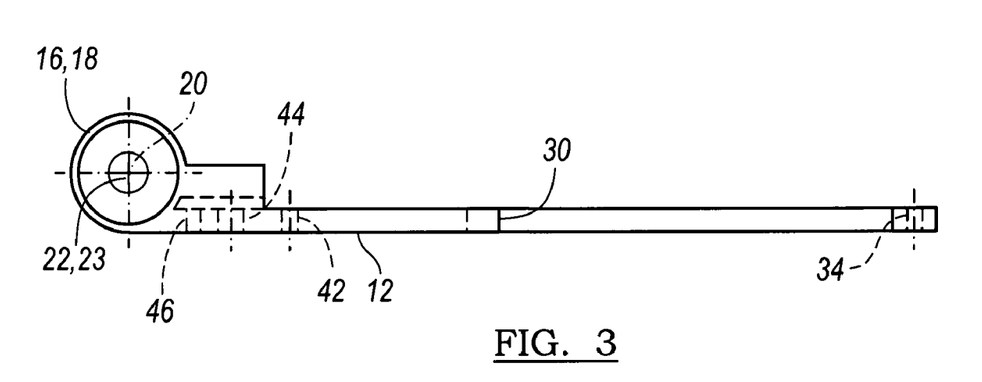
FIG. 3 is a side view of the upper member of FIG. 2.
Figure 4:
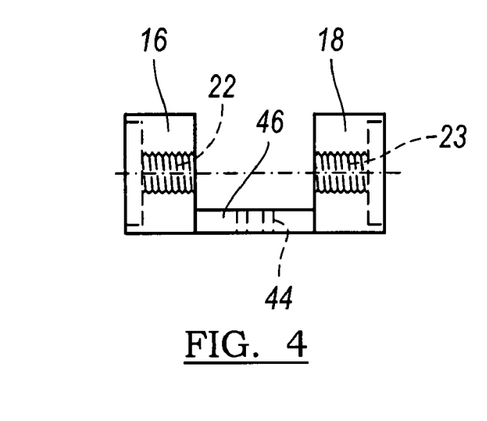
FIG. 4 is an end view of the upper member of FIG. 2.
Figure 5:
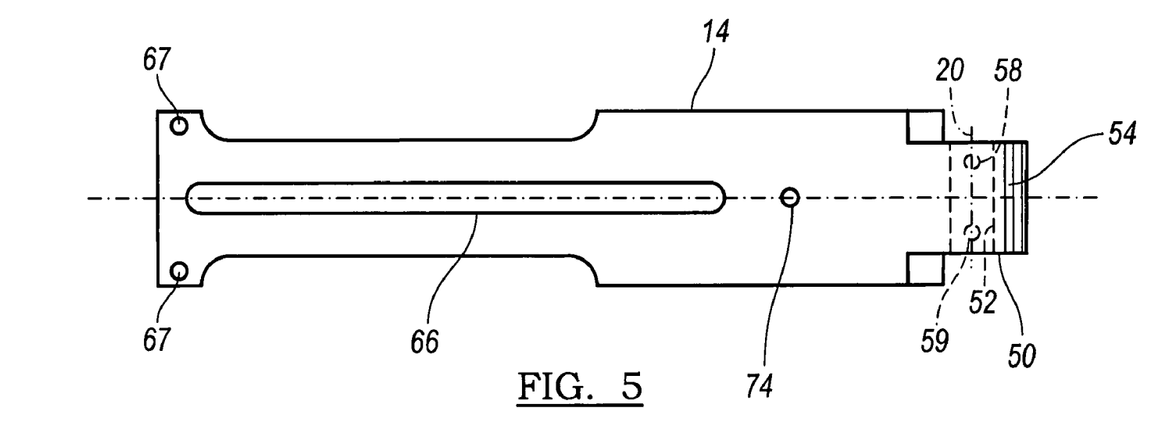
FIG. 5 is a top view of a lower member of the orthotic device of FIG. 1.
Figure 6:
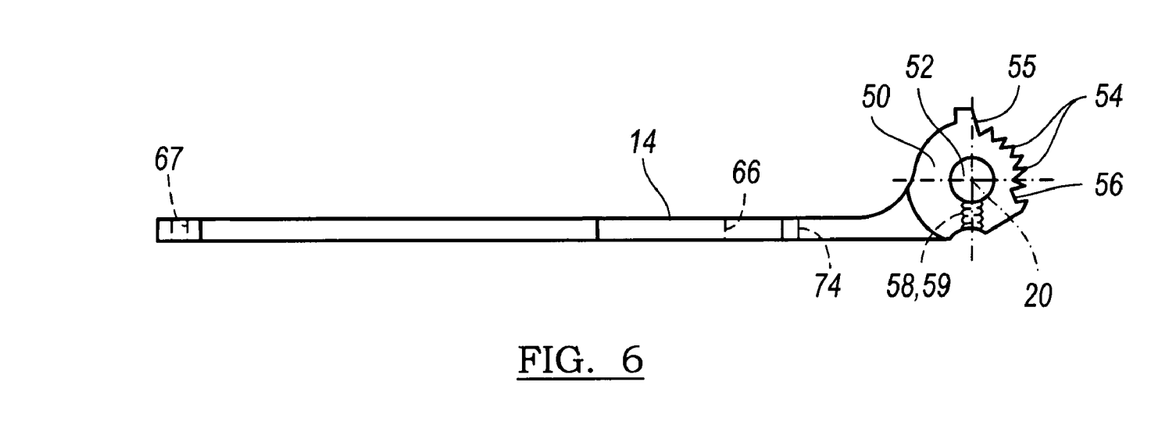
FIG. 6 is a side view of the lower member of FIG. 5.
Figure 7:
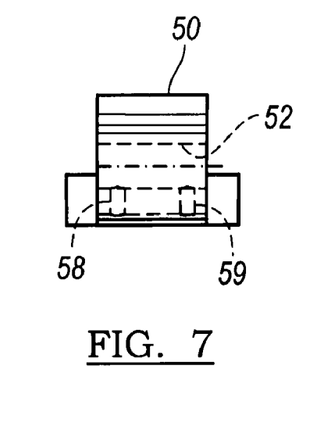
FIG. 7 is an end view of the lower member of FIG. 5.
Figure 8:
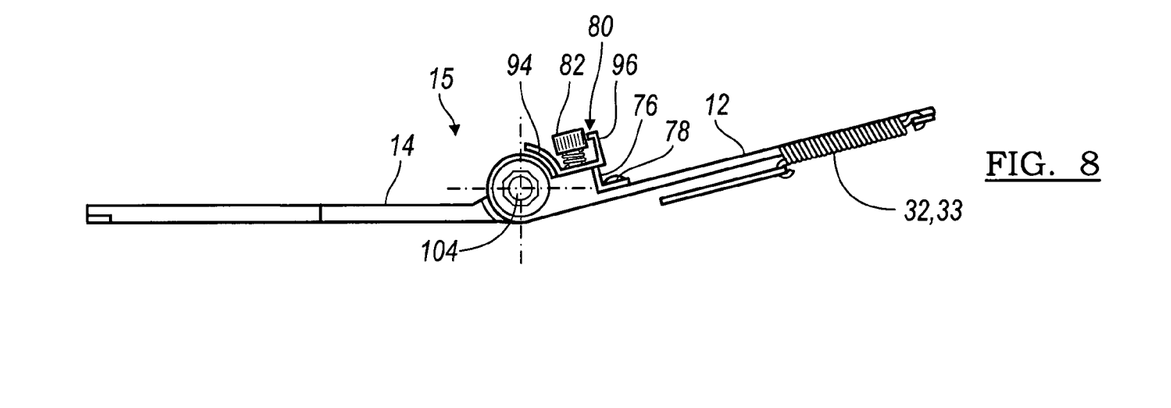
FIG. 8 is a side view of the joint that includes the upper and lower members and a ratchet.
Figure 9:
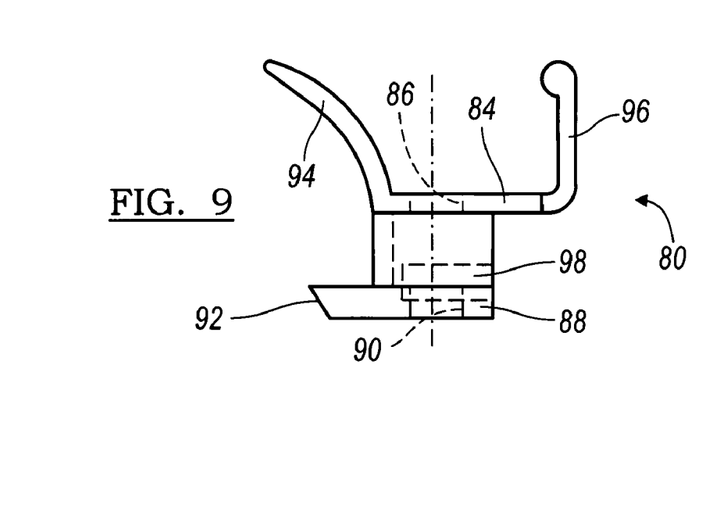
FIG. 9 is a side view of the ratchet of FIG. 8.
Figure 10:
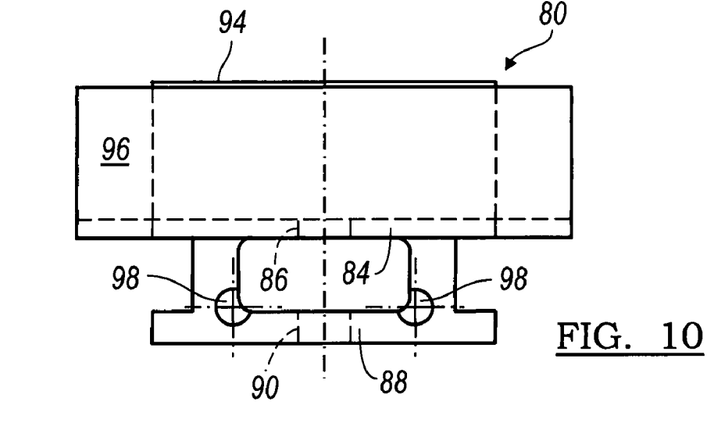
FIG. 10 is a front view of the ratchet of FIG. 8.
Figure 11:
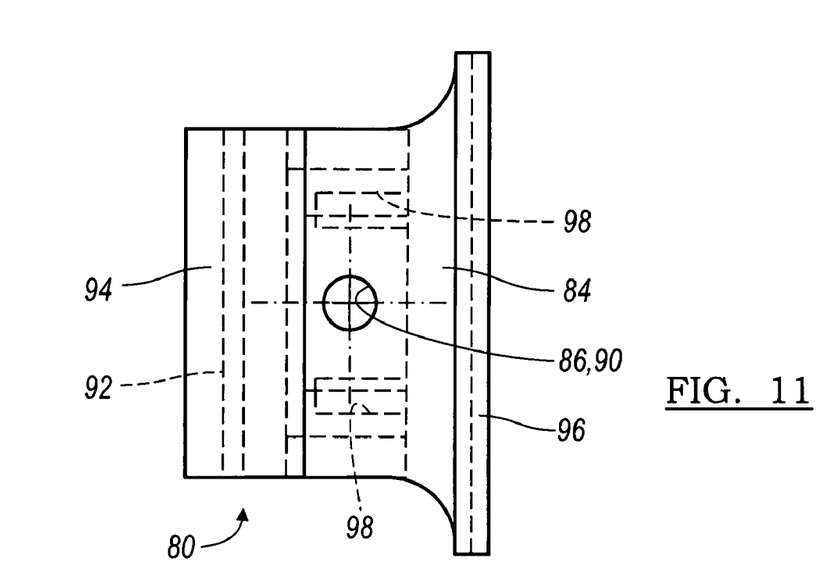
FIG. 11 is a top view of the ratchet of FIG. 8.

FIGS. 1 and 8 show that the ratcheting joint 15 for connecting the upper member 12 and lower member 14 includes an angle stop bracket 76 secured to the upper member 12 by a screw 78 engaged in threaded hole 42, a ratchet 80, and a spring-loaded ratchet lockout pin 82 for securing the ratchet to the upper member 12.

FIGS. 8 through 12 illustrate details of the ratchet 80, which includes an upper plane 84 formed with an unthreaded hole 86; a lower plane 88 formed with an unthreaded hole 90, aligned with hole 86; and a latch 92 for engaging alternately the ratchet teeth 54, stop surface 55, and slot 56 on the lower member 14. A curved arm 94, located at the lower end of the upper plane 84, overlaps the ratchet teeth 54 to protect against an otherwise pinching-point. An adjustment arm 96, located at the upper end of plane 84, provides a surface with which to manually slide ratchet 80 along axis 36 away from the ratchet teeth 54. The ratchet includes two laterally spaced holes 98 directed parallel to axis 36 and closed at their lower ends, each hole 98 containing a compression spring 100. The leg of angle stop bracket 76 bears against one end of springs 100, urging latch 92 toward lug 50 and the ratchet teeth 54.

The spring-loaded ratchet lockout pin 82 is biased outward from holes 86 and 90 by a spring 101, fitted between the head of pin 82 and the outer surface of plane 84. A portion of the shank of pin 82 extends through spring 101 and the aligned holes 86, 90 in the ratchet 80. The threaded shank of pin 82 engages a floating nut 103, which is retained in a space between plane 84 and springs 100 such that the nut 103 cannot rotate when pin 82 is rotated.

Figure 12:
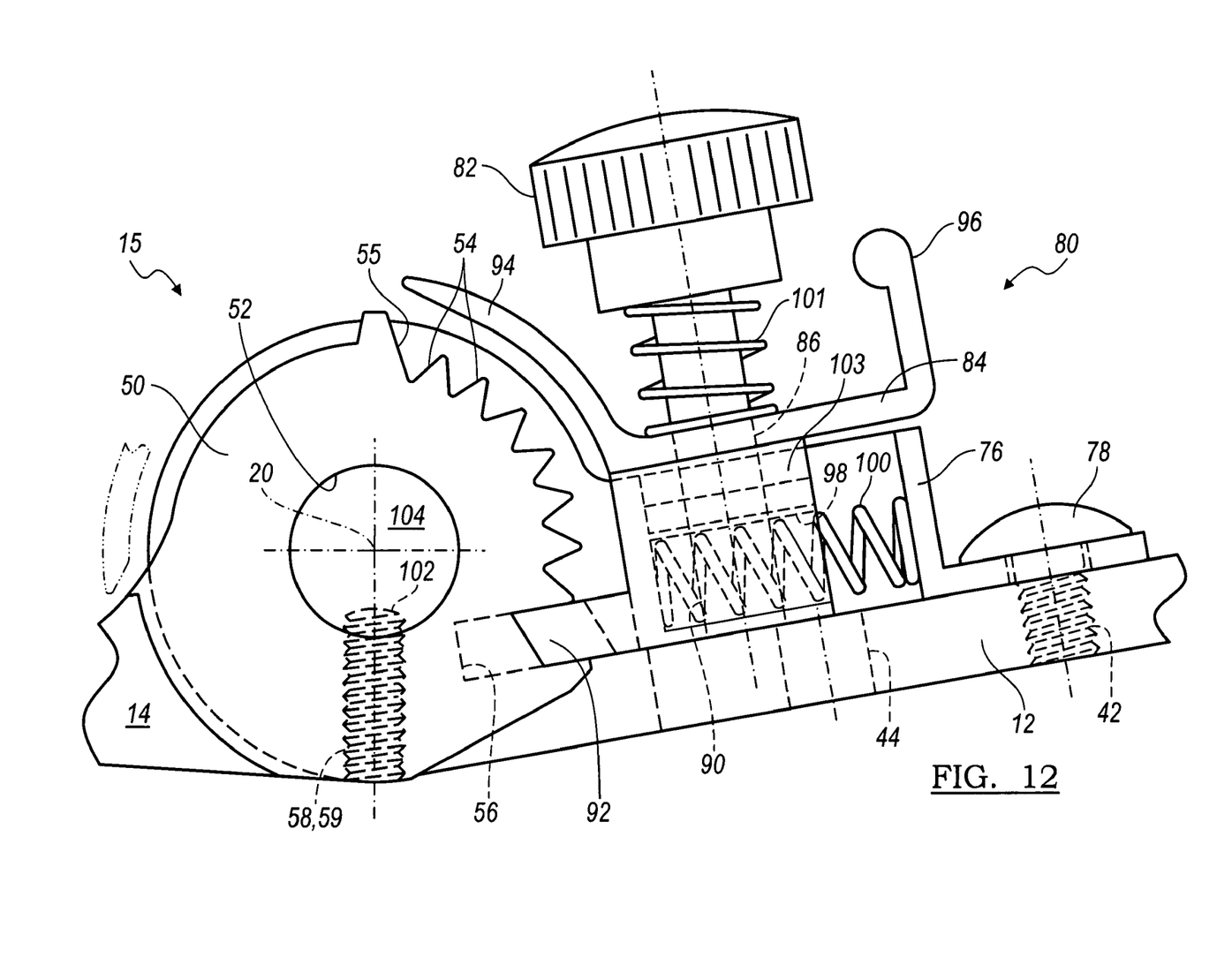
FIG. 12 is a side view of the ratchet joint that connects the upper and lower members.

Ratchet 80 can be moved manually upward along axis 36 against the force of springs 100 to a point where holes 86 and 90 in the ratchet become aligned with hole 44 in the upper member 12. When the ratchet 80 is in that position, it can be more permanently retained there by rotating pin 82 relative to nut 103, thereby driving and securing its shank against the force of spring 101 into elongated hole 44. Ratchet 80 is retained in that position due to contact between the shank of pin 82 and the surface of hole 44. When ratchet 80 is in that position, the ratchet is locked out, i.e. preventing engagement of latch 92 with the ratchet teeth 54 and slot 56 to allow free motion.

The force of springs 100 continually biases ratchet 80 downward toward engagement with the ratchet teeth 54. Ratchet 80 can be returned to the ratcheting position from the lockout position by rotating pin 82 in the opposite direction sufficiently to disengage its shank from nut 103, whereupon ratchet 80 is forced elastically to the ratcheting position by the force of springs 100, i.e. step lock function.

It is important to note that ratchet 80 can be placed temporarily in the lockout position by aligning holes 86, 90 in the ratchet with hole 44 in the upper member 12. Then, without rotating the pin 82 relative to floating nut 103, pin 82 and nut 103 are pushed against the force of spring 101 into hole 44, where ratchet 80 is retained by a frictional reaction force between the shank of pin 82 and the surface of elongated hole 44 due to the force of springs 100.

In summary, therefore, with view of FIG. 12, the shank of ratchet lockout pin 82 is engaged with nut 103 and the holes 86, 90 of ratchet 80. The ratchet is moved upward along axis 36 in opposition to the force of springs 100 to the ratchet lockout position, where pin 82 enters the elongated hole 44 in the upper member 12. In the ratchet lock out position, latch 92 is disengaged from ratchet teeth 54 and slot 56 on the lower member 14. Upon moving pin 82 out of hole 44, ratchet 80 is forced downward by springs 100 such that latch 92 ratchets on or engages with the ratchet teeth 54, or engages the stop surface 55 or enters the slot 56 on lug 50 of the lower member 14.

Further, FIG. 12 shows a set screw 102 threaded into hole 58 and engaged with the shank of a headless bolt 104, whose right-hand screw threads are engaged with the threaded holes 22, 23 in lugs 16, 18, respectively, of the upper member. Bolt 104 passes through the unthreaded hole 52 in the lug 50 of the lower member 14. A similar set screw 102 is threaded into hole 59 and engaged with bolt 104. The set screws 102 prevent rotation of bolt 104 relative to lug 50 about axis 20, so as to create axial rotation of bolt 104 along axis 20 in joint 15 by pivoting the lower member 14 relative to upper member 12.

Figure 13:
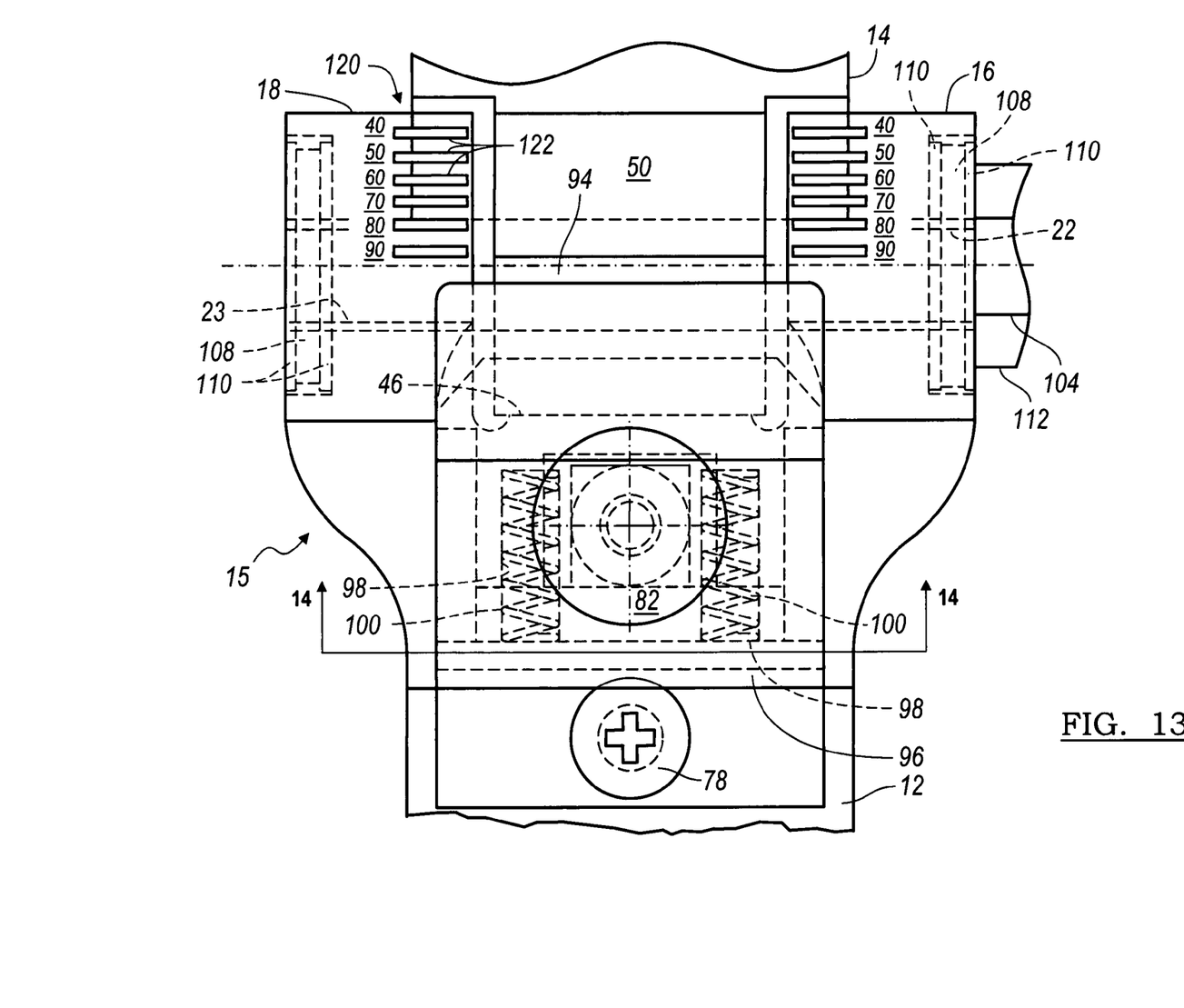
FIG. 13 is a top view of the ratchet joint of FIG. 12.
Figure 14:
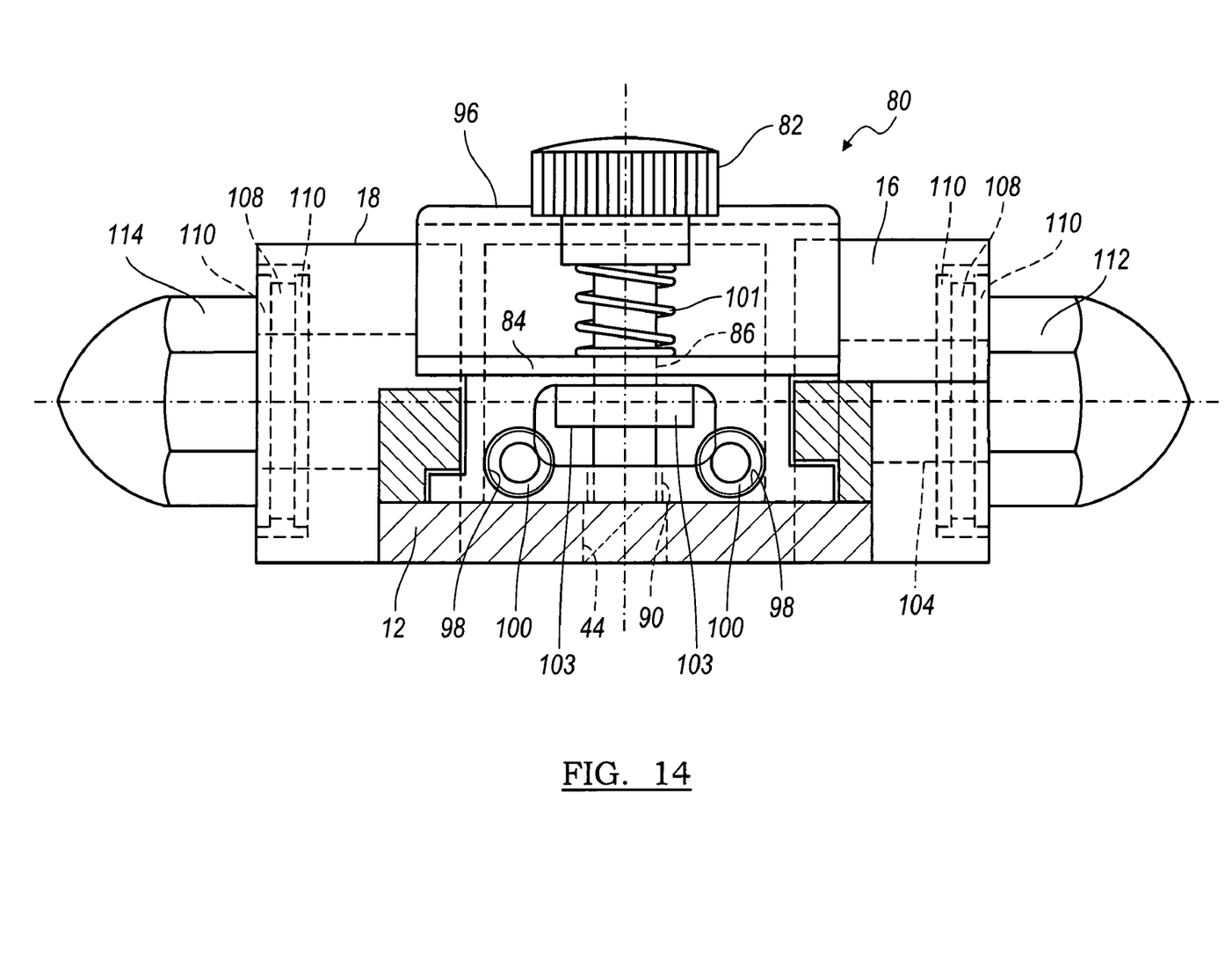
FIG. 14 is a cross section taken at plane 14-14 of FIG. 13.

Focusing now on FIGS. 1, 13 and 14, a thrust bearing 108 and washers 110, located on opposite sides of the thrust bearing, are fitted in the counterbore formed in the outer surface of lugs 16, 18 to facilitate loosening and tightening lock nuts 112, 114 on the threads of bolt 104.

As FIG. 13 illustrates, the surfaces of the lugs 16, 18 of the upper member 12 include a scale 120 of graduated angular positions or witness marks 122. The scaled witness marks 122 correspond to the angular displacement of the joint 15 from a reference angular position, i.e., the straight-out position of the leg, in which members 12 and 14 are aligned substantially parallel to axis 36. Latch 92 can engage the respective ratchet tooth 54 that corresponds to the selected angular position.

In operation, the joint 15 is able to pivot about the lateral axis 20 and the brace 10 can provide multiple functions, as described below:

1. To activate the ratchet 80, the ratchet lockout pin 82 is turned counterclockwise relative to nut 103 several revolutions until the ratchet releases. The ratchet 80 can be locked again by retracting ratchet 80 and turning the ratchet lockout pin 82 several turns clockwise.

To lock out the ratchet 80 on a temporary basis, such as when the person using the brace 10 is sitting down, ratchet 80 is retracted to the stop bracket 76 and the ratchet lockout pin 82 is pushed toward the back of the leg, which causes the shank of pin 82 to enter hole 44 where it is retained by the force of springs 100 in a friction hold position. Pin 82 is held in, thereby releasing ratchet 80. The ratchet 80 will lock automatically when the brace 10 returns to the straight position, i.e., the drop lock function. The ratchet 80 can also be reengaged by applying slight upward pressure on the ratchet to release the friction hold position.

2. When ratchet 80 is locked out on a temporary basis as described above, it will automatically release when slot 56 is contacted, slightly pushing latch 92, causing the shank of pin 82 to briefly move away from the wall of hole 44, whereby spring 101 forces upward the lockout pin 82 to disengage. Then, in the released position, the ratchet will automatically lock when the leg reaches the straight position, i.e. full extension. Once the ratchet is released from the temporary lockout position when the leg is contracted at the knee, the ratchet will lock and stop contracture every 10° to 20°, i.e. the distance between successive ratchet teeth, until the leg reaches the straight position, whereupon the brace 10 will not allow contracture or extension due to engagement of latch 92 in slot 56. Preferably, the distance between successive ratchet teeth corresponds to about 15°.

3. The joint 15 can rotate freely (i.e. free motion function) or be set to a particular range of motion (i.e. range of motion function), with or without ratcheting (which is described in more detail below) upon loosening or tightening lock nuts 112 and 114 about bolt 104. By adjusting the lock nuts 112, 114, the range of motion of brace 10 is changed about the lateral axis 20. More specifically, as upper member 12 rotates about bolt 104 (which is secured to lower member 14 by set screws 102 at center lug 50), lugs 16, 18 move up and down axis 20 by their threadable engagement with bolt 104 at threaded holes 22, 23, respectively, until either lug 16 contacts lock nut 112 or lug 18 contacts lock nut 114. At that point, the range of motion stops.

By adjusting lock nuts 112 and 114 along bolt 104, the pivotal range of motion between lower member 14 and upper member 12 can be changed or locked to best accommodate the several stages of therapy. More specifically, with ratchet 80 locked out permanent or temporarily as described above, the brace 10 can be adjusted to provide a range of motion. With brace 10 in the straight position, both lock nuts 112, 114 are tightened. The joint 15 is then locked and allows no rotary movement about axis 20. If, for example, a flexion limit angle of 20° is desired, lock nut 112 is loosened, and the joint 15 can then be pivoted through an angle of approximately 20°, in the direction that reduces the magnitude of the angle between the thigh and the calf. The desired flexion limit angle can be checked with reference to the witness marks 122 located near the lock nuts 112, 114 on lugs 16, 18. Lock nut 112 can be adjusted to precisely set the desired flexion limit angle.

If a combination of flexion and extension is desired, the flexion limit angle is set first by adjusting lock nut 114, as described above. Then, the extension angular limit is set by tightening lock nut 112. The desired extension limit angle can be checked with reference to the witness marks 122 located near the lock nuts 112, 114 on lugs 16, 18. Lock nut 112 can be adjusted to precisely set the desired extension limit angle. The brace 10 is returned to the free motion function upon loosening both lock nuts 112, 114 about one-half turn.

4. The brace 10 can also be adjusted to select a desired angular position without pivoting in either direction. To accomplish this, lock nuts 112, 114 are loosened about one-half turn and, with ratchet 80 locked out permanent or temporarily as described above, joint 15 is pivoted about axis 20 to the desired angular position, and the lock nuts are retightened, thereby relocking joint 15 at the desired position (i.e. variable, fixed position function).

Finally, it is important to note that with this orthotic device being mounted to the posterior portion of an appendage, as the joint flexes, contraction of the muscles and skin occurs. Therefore, with this knee orthotic, for example, the thigh cuff 24 and calf cuff 60 are positioned and firmly secured by VELCRO straps 38, 40 and 70, 72, respectively, to the leg and back of the knee. In order to accommodate contraction and expansion of the muscles and skin that accompany flexion and extension of the knee joint, therefore, upper member 12 slides along axis 36 in upper pocket 26 and lower member 14 slides along the axis 36 in the longitudinal lower pocket 62, while the positions of the thigh cuff 24 and calf cuff 60 relative to the leg remain unchanged. As a result, the location of joint 15 remains unchanged at the back of the knee due to the tendency of springs 32, 33, 68, 69 to allow the thigh cuff 24 and calf cuff 60 to dynamically reposition relative to the joint 15.

Figure 15:
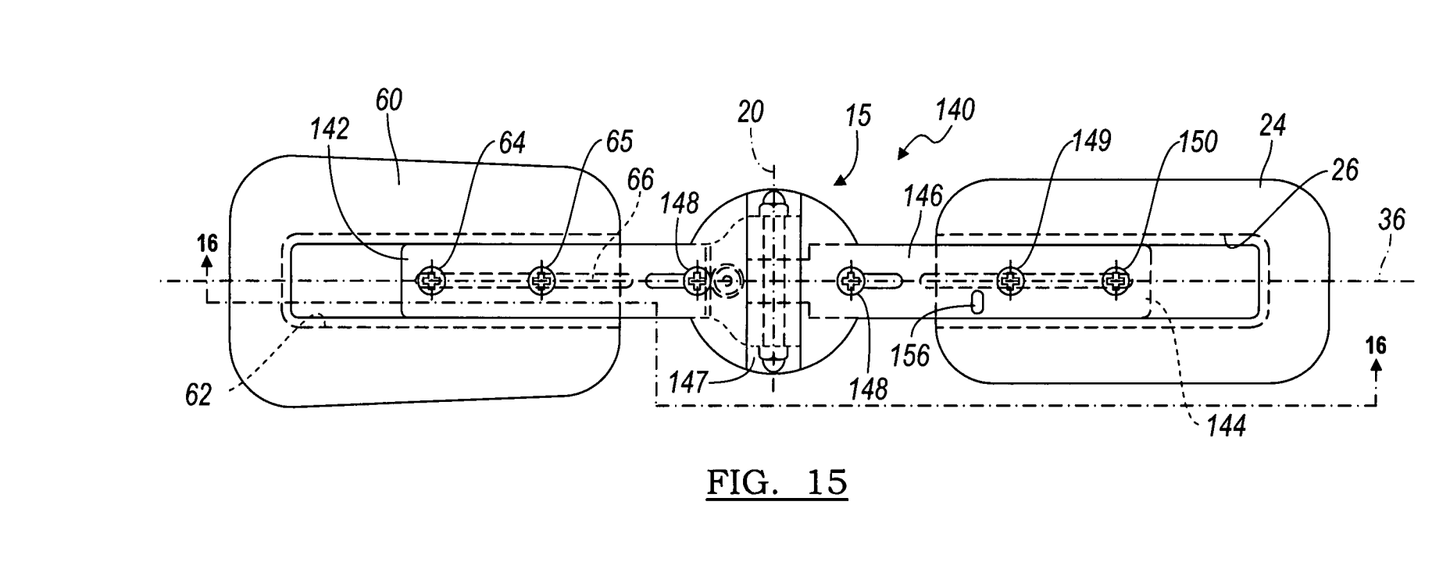
FIG. 15 is a rear view of an alternate embodiment of a multiple function leg orthotic device shown in FIG. 1.
Figure 16:
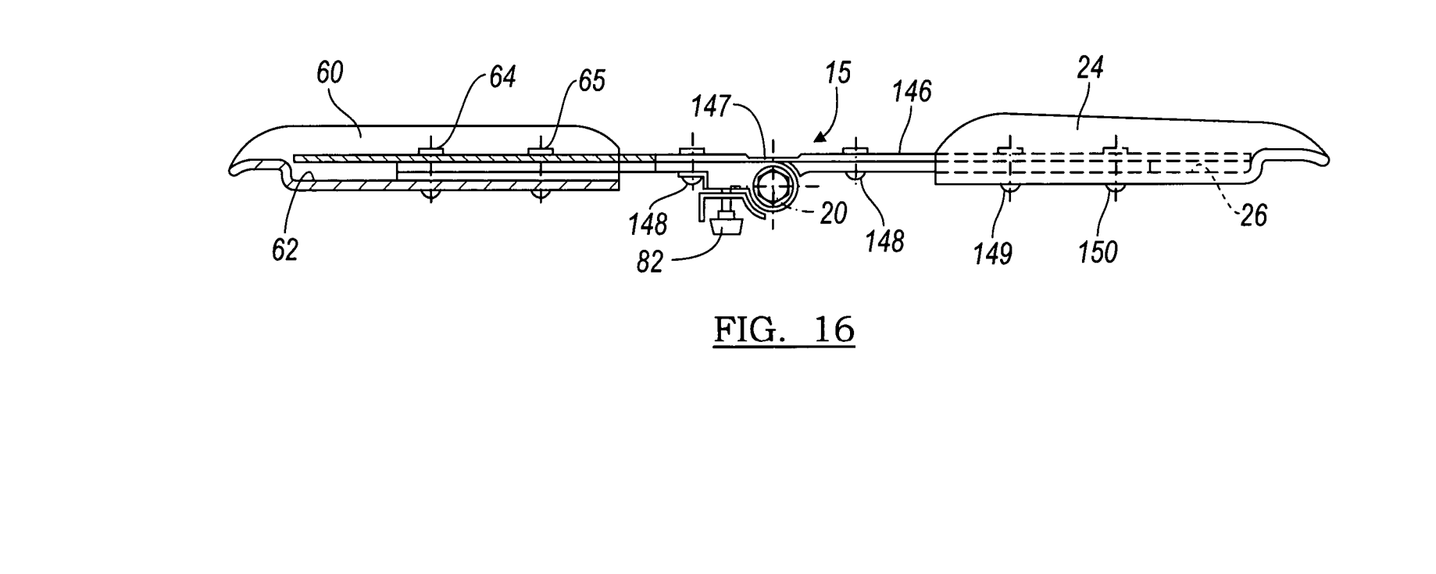
FIG. 16 is a side view, partially cross sectioned at plane 16-16, of the orthotic device of FIG. 15.
Figure 17:
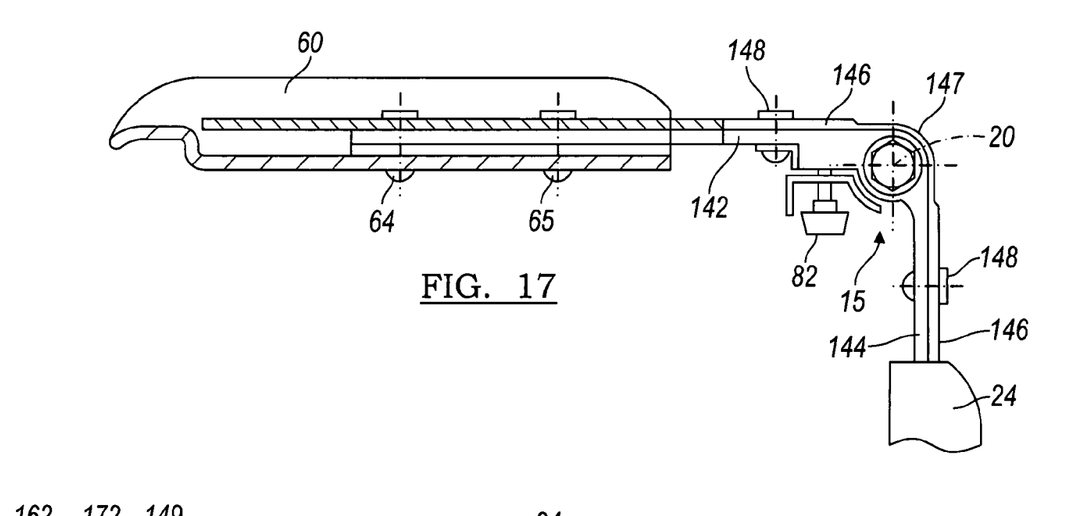
FIG. 17 is a side view showing the orthotic device of FIGS. 15 and 16 in the flexion position.

FIGS. 15 and 16 illustrate an alternate embodiment of an orthotic device 140 in the fully extended position, and FIG. 17 shows orthotic device 140 in the flexion position, fully pivoted about axis 20 of the ratcheting joint 15, described above with reference to FIGS. 1-14. The orthotic device 140 includes a lower member 142 and upper member 144, which are interconnected by the ratcheting joint 15. The VELCRO straps 38, 40, 70, 72 of FIG. 1 are not illustrated.

The cuffs 24, 60 are preferably strapped to an appendage of the human body on opposite sides of a joint at which the appendage pivots. For example, the lower cuff 60 may support the forearm or calf, and the upper cuff 24 may support the upper arm or thigh, respectively.

A flexible strap 146, fitted in the pockets 26, 62 of the upper cuff 24 and lower cuff 60, respectively, extends longitudinally on the inner side of the device in contact with the user's leg or arm, or clothing covering the leg or arm. The thickness of a first portion 147 of strap 146 may be reduced locally in the vicinity of axis 20, thereby reducing its flexural stiffness and facilitating bending between the flexion position of FIG. 17 and the extended position of FIG. 16. Due to strap 146 being located eccentric of the axis 20, when the orthotic device 140 pivots from the extended position of FIG. 16, an upper portion of strap 146, spaced along member 144 from axis 20, is used to actuate a mechanism that draws the upper cuff 24 toward axis 20. Preferably, strap 146 is formed of a material sized both (i) to permit its flexure at the reduced thickness first portion 147 due to a moderate force tending to pivot the device 140 about axis 20, and (ii) to prevent its buckling or compressive instability in the vicinity of cuffs 24, 60 due to the strap transmitting force along its length to actuate the cuffs. A strap of woven fabric would likely be unsuitable, but a strap of bendable plastic or a light metal is suitable for this purpose.

Threaded attachments 64, 65 secure belt cuff 60 to lower member 142, and threaded attachments 149, 150 secure cuff 24 to upper member 144. Attachments 148 are secured to the lower and upper members 142, 144 and pass through a slotted hole in strap 146 to stabilize the strap from buckling away and to accommodate movement of the strap, relative to the members 142, 144 as the device 140 pivots about axis 20.

Figure 18:
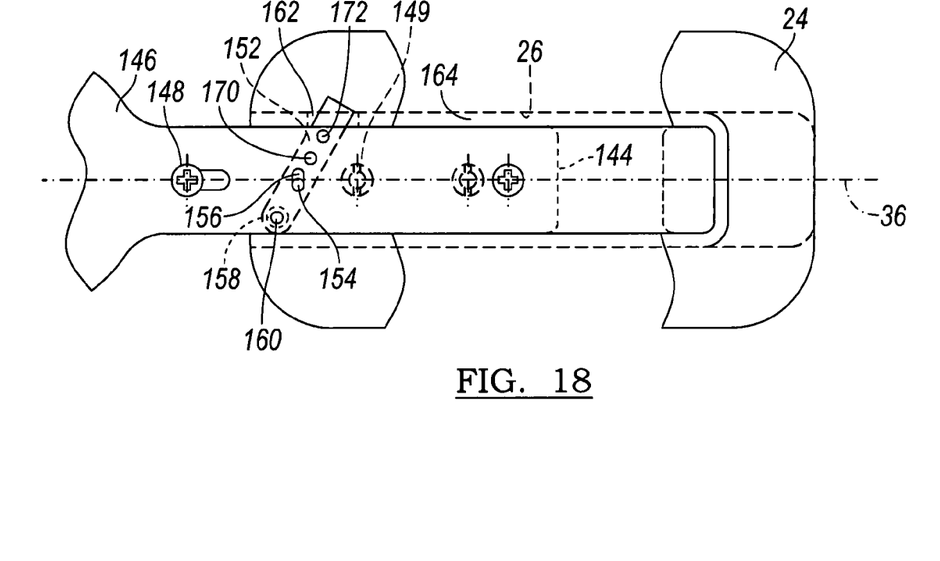
FIG. 18 is a rear view of a cuff actuation mechanism for the orthotic device of FIG. 15.
Figure 19:
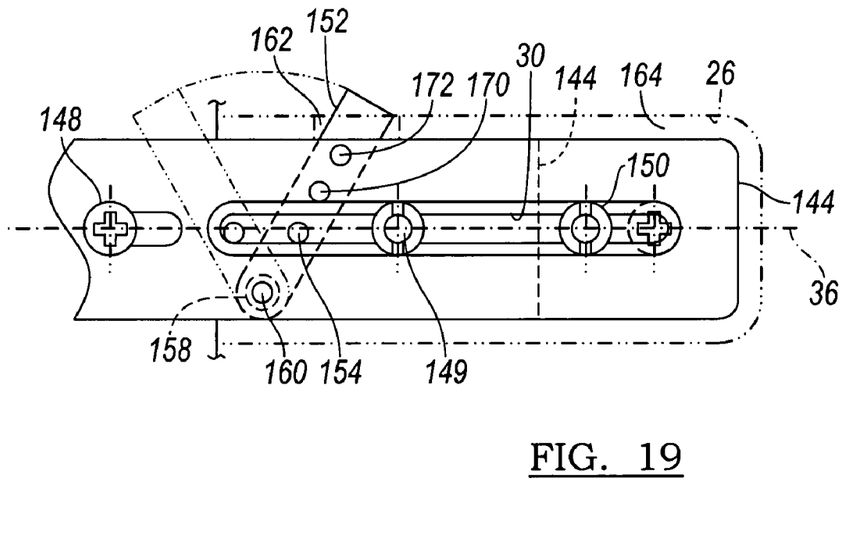
FIG. 19 is a rear view showing the range of travel of the cuff actuation lever of FIG. 18.
Figure 20:
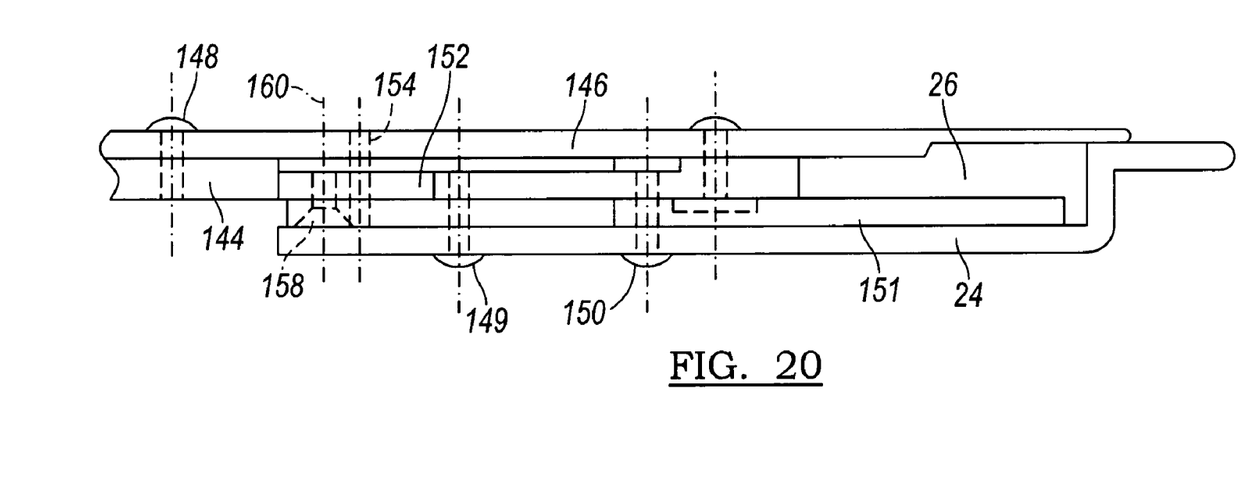
FIG. 20 is a side view of a second cuff actuation mechanism of FIGS. 18 and 19.

The mechanism illustrated in FIGS. 18, 19 and 20 actuates the upper cuff 24 toward axis 20 in response to pivoting the orthotic device 140 between the extended and flexion positions due to flexure of strap 146 caused by the device pivoting. A lever 152 carries a pin 154, which extends laterally from the lever into a hole 156 formed in strap 146. Lever 152 is secured to upper member 144 by a rivet 158, about whose axis 160 the lever pivots in response to leftward and rightward longitudinal movement of strap 146 as the device 140 pivots about axis 20. Lever 152 extends through a slotted hole 162 formed through the wall 164 of the pocket 26 of upper cuff 24. Attachments 149, 150 extend through the slot 30 in upper member 144, thereby maintaining strap 146 aligned with member 144. A spacer 151 is located in the pocket 26 of cuff 24.

In operation, when the orthotic device 140 pivots about axis 20 from the extended position of FIGS. 15 and 16 to the flexion position of FIG. 17, the length of the strap 146 that is spaced from axis 20 tends to move toward axis 20 relative to cuff 24 due to device 140 pivoting about axis 20. Pin 154, however, moves toward axis 20 as strap 146 flexes about axis 20. This movement of pin 154 causes lever 152 to pivot counterclockwise about axis 160, when viewed as in FIGS. 18 and 19, thereby moving upper cuff 24 leftward along slot 30 a greater distance than the distance pin 154 travels. Preferably, upper cuff 24 moves about 2.5 times further than pin 154 moves, when the pin moves about 0.50 inches.

When the orthotic device 140 returns to the extended position of FIG. 15 by pivoting about axis 20, pin 154 articulates away from axis 20, causes lever 152 to pivot clockwise about axis 160, and moves the upper cuff 24 rightward along slot 30 a greater distance than the distance pin 154 travels. These movements of cuff 24 help to control movement of the body joint (whether a knee or elbow) spanned by the device 140.

In addition to hole 156, lever 152 may have a series of holes 170, 172 mutually spaced along the length of the lever, permitting movement of the upper cuff 24 in response to a given displacement of strap 146 to vary depending on which the of holes 156, 170, 172 pin 154 engages.

A second mechanism for actuating the upper cuff 24 in response to pivoting of the orthotic device 140 between the extended and flexion positions of FIGS. 16 and 17, respectively, is described next with reference to FIGS. 21 through 24. The threaded attachments 149, 150 extend through the slot 30 in upper member 144.

Gear teeth 180, 182 are formed in the wall 164 of the pocket 26 of the upper cuff 24. Gear teeth 184, 186, facing gear teeth 180, 182, respectively, are formed in the upper member 144. A gear 188, meshing with gear teeth 180 and 184, is secured to strap 146 by attachment 190. Similarly, a gear 192, meshing with gear teeth 182 and 186, is secured to strap 146. A spacer 194, fitted in pocket 26, is formed with a slot 196, aligned with slot 30, and with recesses 198, 200, which provide space for the gears 188, 192.

Figure 21:
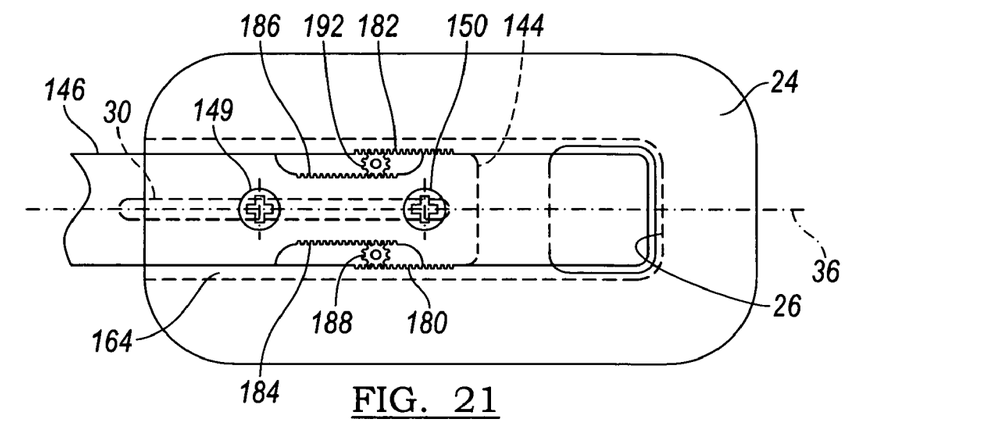
FIG. 21 is a rear view of the second cuff actuation mechanism for the orthotic device of FIG. 15.
Figure 22:
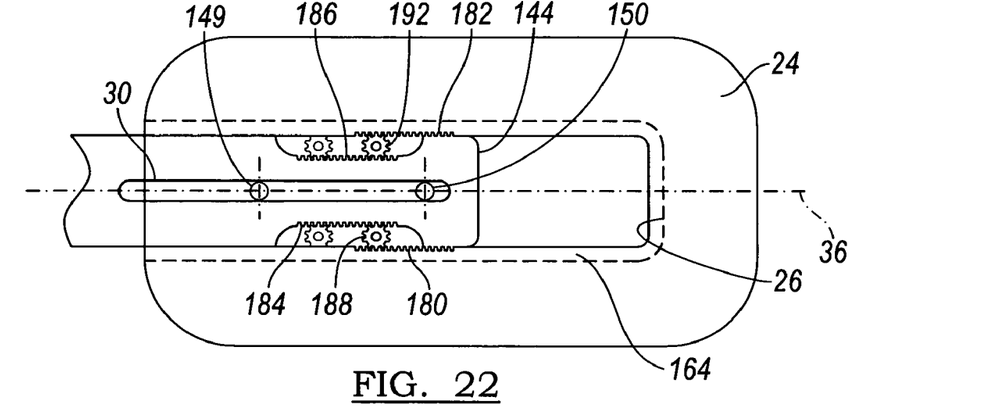
FIG. 22 is a rear view of the cuff actuation mechanism of FIG. 21 with the strap removed.
Figure 23:
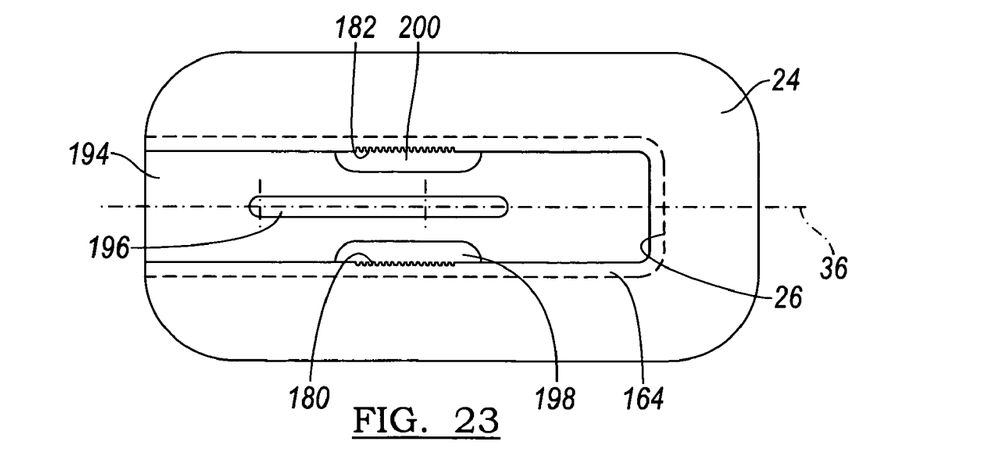
FIG. 23 is a rear view of the cuff and spacer of the cuff actuation mechanism of FIG. 21.
Figure 24:
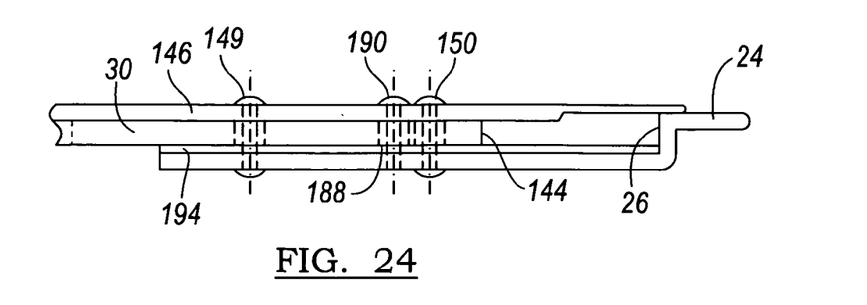
FIG. 24 is a side view of the cuff actuation mechanism of FIGS. 21 and 22.

In operation, when the orthotic device 140 pivots about axis 20 from the extended position to the flexion position, the length of the strap 146 that is spaced from axis 20 portion tends to move toward axis 20 relative to cuff 24 due to the device 140 pivoting about axis 20. Gears 188, 192 move toward axis 20 as strap 146 flexes about axis 20, causing gear 192 to rotate counterclockwise and gear 188 to rotate clockwise, when viewed as shown in FIGS. 21 and 22. Rotation of gears 188 and 192 moves upper cuff 24 leftward along slot 30 toward axis 20 a greater distance than the distance strap 146 and gears 188, 192 travel toward axis 20. Preferably, gears 188, 192 are sized to move upper cuff 24 about 1.0 inch when the gears move about 0.50 inches.

When the orthotic device 140 returns to the extended position of FIG. 15 by pivoting about axis 20, the upper portion of strap 146 moves gears 188, 192 away from axis 20. This movement causes gear 188 to rotate counterclockwise, gear 192 to rotate clockwise, and upper cuff 24 to move rightward along slot 30 a greater distance than the distance the gears 188, 192 are displaced from axis 20. These movements of cuff 24 help to control movement of the joint (whether a knee or elbow) spanned by the device 140.

Figure 25:
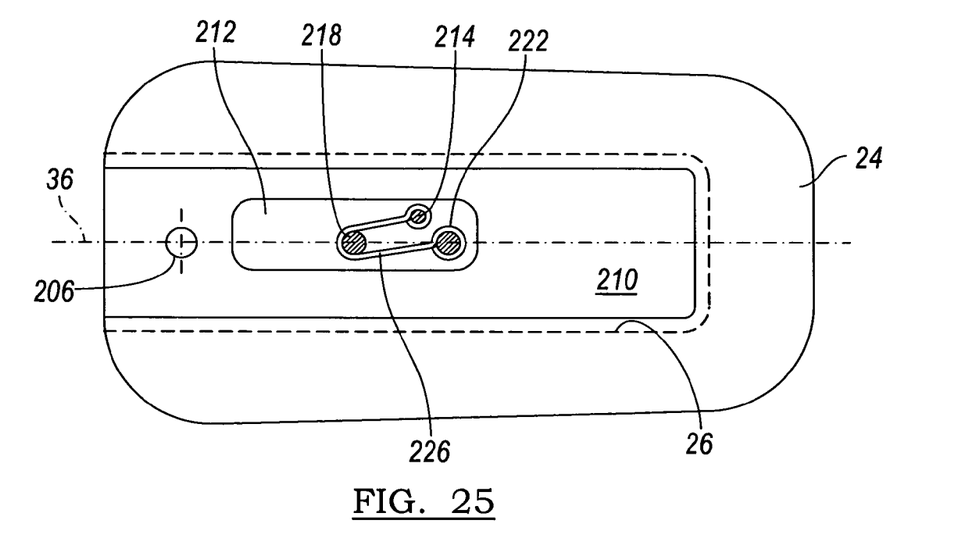
FIG. 25 is a rear view taken at plane 25-25 in FIG. 26 showing a third cuff actuation mechanism for the orthotic device of FIG. 15.
Figure 26:
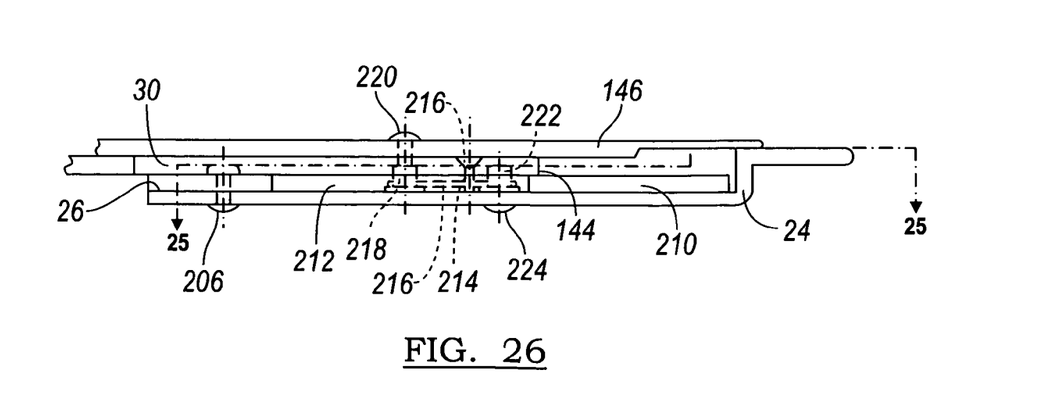
FIG. 26 is a side view of the cuff actuation mechanism of FIG. 25.

A third mechanism for actuating the upper cuff 24 in response to pivoting of the orthotic device 140 between the extended and flexion positions of FIGS. 16 and 17, respectively, is described next with reference to FIGS. 25 and 26.

Threaded attachment 206 secures a spacer 210, fitted in the pocket 26 of the upper cuff 24, to the upper cuff 24. The spacer 210 is formed with a recess 212, which is aligned with the central slot 30 formed in the upper member 144. The shank 214 of a rivet 216, secured to upper member 144, extends into the recess 212. A pin 218, secured by fastener 220 to the strap 146, and a pin 222, secured by fastener 224 to the upper cuff 24, are also located in the recess 212 of the spacer 210. One end of a wire or thin cable 226 loops around and is secured to the shank 214 of rivet 216, and the other end of the cable 226 loops around and is secured to pin 222. The cable 226 also loops around, but is not secured to pin 218.

In operation, when the orthotic device 140 pivots about axis 20 from the extended position of FIG. 15 to the flexion position shown in FIG. 17, the strap 146 moves pin 218 leftward toward axis 20, thereby developing tension in the cable 226 because the rivet 214 is fixed to the upper member 144, which does not move relative to axis 20. A tension force is applied by cable 226 to pin 222, causing pin 222 and the upper cuff 24 to move as a unit leftward toward axis 20. Pin 222 and upper cuff 24 are displaced about two times the distance that pin 218 and strap 146 travel toward axis 20. Preferably when the orthotic device 140 is fully pivoted, pin 218 and strap 146 travel toward axis 20 about 0.50 inches and pin 222 and upper cuff 24 are displaced about 1.0 inches toward axis 20.

Although the cuff actuation mechanisms illustrated in FIGS. 18 through 26 are described with respect to actuating the upper cuff 24 as the orthotic device 140 pivots between the flexion and extended positions, the lower cuff 60 may be similarly actuated by any of the mechanisms, or any combination thereof, concurrently with the upper cuff 24, or the lower cuff 60 may be so actuated instead of the upper cuff 24.

It should be noted that the present invention can be practiced otherwise than as specifically illustrated and described, without departing from its spirit or scope. It is intended that all such modifications and alterations be included insofar as they are consistent with the objectives and spirit of the invention.

What is claimed is:

1. An orthotic device for a joint of a human body at which a body appendage pivots, comprising:
   a first member located on a first side of the joint;
   a second member located on a second side of the joint opposite the first side;
   a connection joining the first member and the second member and having an oriented axis about which the members pivot toward a flexion position and extended position;
   a cuff spaced from the axis; and
   a mechanism having an actuator for displacing the cuff along one of the members while moving toward the flexion or extended position in response to pivoting the device at the connection.

2. The orthotic device of claim 1, wherein the actuator comprises:
   a strap that actuates the mechanism to move the cuff toward the axis as the device pivots toward the flexion position, wherein the mechanism moves the cuff toward the axis through a distance greater than a displacement toward the axis of a portion of the strap that is spaced from the axis.

3. The orthotic device of claim 1, wherein the actuator comprises:
   a strap that actuates the mechanism to move the cuff away from the axis as the device pivots toward the extended position, wherein the mechanism moves the cuff away from the axis through a distance greater than a displacement from the axis of a portion of the strap that is spaced from the axis.

4. The orthotic device of claim 1, wherein the actuator comprises:
   a strap including a first portion extending across the connection that bends when the device pivots about the axis, and a second portion spaced from the first portion and actuating the mechanism along said one of the members as the device pivots, so that the mechanism moves the cuff in response to the strap, wherein a cuff displacement distance is greater than a displacement distance of the second portion of the strap.

5. The orthotic device of claim 1, wherein:
   the mechanism further includes a lever secured to said one of the members, said lever engages the cuff at a first distance spaced from a pivot of the lever, and the lever being engaged with a strap at a second distance spaced from the pivot of the lever, and the strap actuating the lever through a displacement relative to said one of the members as the device pivots about the connection.

6. The orthotic device of claim 5, wherein the first distance is greater than the second distance.

7. The orthotic device of claim 1, wherein the actuator comprises:
   a strap moving through a displacement relative to said one of the members as the device pivots about the connection; and
   wherein the mechanism includes a gear displaced by the strap, the gear being supported for rotation and meshing with said one of the members and the cuff.

8. The orthotic device of claim 1, wherein the actuator comprises:
   a strap moving through a displacement relative to said one of the members as the device pivots about the connection; and
   wherein the mechanism further includes:
      a first gear displaced by the strap at a first lateral side of a longitudinal axis, and the first gear being supported for rotation and meshing with said one of the members and the cuff; and
      a second gear displaced by the strap at a second lateral side of the longitudinal axis, and the second gear supported for rotation and meshing with said one of the members and the cuff.

9. The orthotic device of claim 8, wherein the gears are sized such that the cuff is displaced along the longitudinal axis through a distance greater than the displacement of the strap.

10. The orthotic device of claim 1, wherein the actuator comprises:
    a strap moving through a displacement relative to said one of the members as the device pivots about the connection; and
    wherein the mechanism further includes:
       a first pin secured to said one of the members;
       a second pin engaged with the strap;
       a third pin secured to the cuff; and
       a cable secured to the first pin, extending from the first pin to the second pin, looping around the second pin, and extending to and secured to the third pin.

11. The orthotic device of claim 1, wherein the cuff is located for engagement with the appendage at a lower side of the joint.

12. The orthotic device of claim 1, wherein the cuff is located for engagement with the appendage at an upper side of the joint.

13. An orthotic device for a joint of a human body at which a body appendage pivots, comprising:
    a first member located on a first side of the joint;
    a second member located on a second side of the joint opposite the first side;
    a connection joining the first member and the second member and having an axis about which the members pivot;
    a first cuff spaced from the axis;
    a second cuff spaced from the axis;

a first mechanism for displacing the first cuff along the first member in response to the device pivoting at the connection; and a second mechanism for displacing the second cuff along the second member relative to the axis in response to the device pivoting at the connection.

14. The orthotic device of claim 13 further comprising:
a strap that actuates the first mechanism toward the axis through a first displacement as the device pivots, the first mechanism moving the first cuff in response to the displacement toward the axis through a distance greater than the first displacement, and wherein the strap actuates the second mechanism toward the axis through a second displacement as the device pivots, and the second mechanism moving the second cuff in response to the second displacement toward the axis through a distance greater than the second displacement.

15. An orthotic device for a joint of a human body at which a body appendage pivots, comprising:
a first member located on a first side of the joint;
a second member located on a second side of the joint opposite the first side;
a connection joining the first member and the second member and having an axis about which the members pivot;
a cuff spaced from the axis;
a strap that flexes as the device pivots including a portion that moves through a displacement along the first member relative to the axis in response to said flexure; and
a mechanism engaged with the strap portion and the cuff, actuated by said displacement, and moving the cuff through a distance greater than the displacement.

16. The orthotic device of claim 15, wherein:
the strap actuates the mechanism toward the axis as the device pivots toward a flexion position, and the mechanism moves the cuff toward the axis in response to the displacement of the strap.

17. The orthotic device of claim 15, wherein:
the strap actuates the mechanism away from the axis as the device pivots toward an extended position, and the mechanism moves the cuff away from the axis in response to the displacement of the strap.

18. The orthotic device of claim 15, wherein:
the mechanism includes a lever secured to the first member, and the lever being engaged with the cuff at a first distance spaced from a pivot of the lever and engaged with the strap at a second distance spaced from the pivot of the lever.

19. The orthotic device of claim 15, wherein the first distance is greater than the second distance.

20. The orthotic device of claim 15, wherein:
the mechanism includes a gear secured to and displaced by the strap, supported for rotation, and meshing with the first member and the cuff.

21. The orthotic device of claim 15, wherein the mechanism further includes:
a first gear secured to the strap at a first lateral side of a longitudinal axis, supported for rotation, and meshing with the first member and the cuff; and
a second gear secured to the strap at a second lateral side of the longitudinal axis, supported for rotation, and meshing with said first member and the cuff.

22. The orthotic device of claim 15, wherein the mechanism further includes:
a first pin secured to said one of the members;
a second pin secured to the strap;
a third pin secured to the cuff; and
a cable secured to the first pin, extending from the first pin to the second pin, looping around the second pin, and extending to and secured to the third pin.

* * * * *